May 26, 1959 R. V. LINDQUIST Plant Pat. 1,836
ROSE PLANT
Filed Oct. 31, 1958
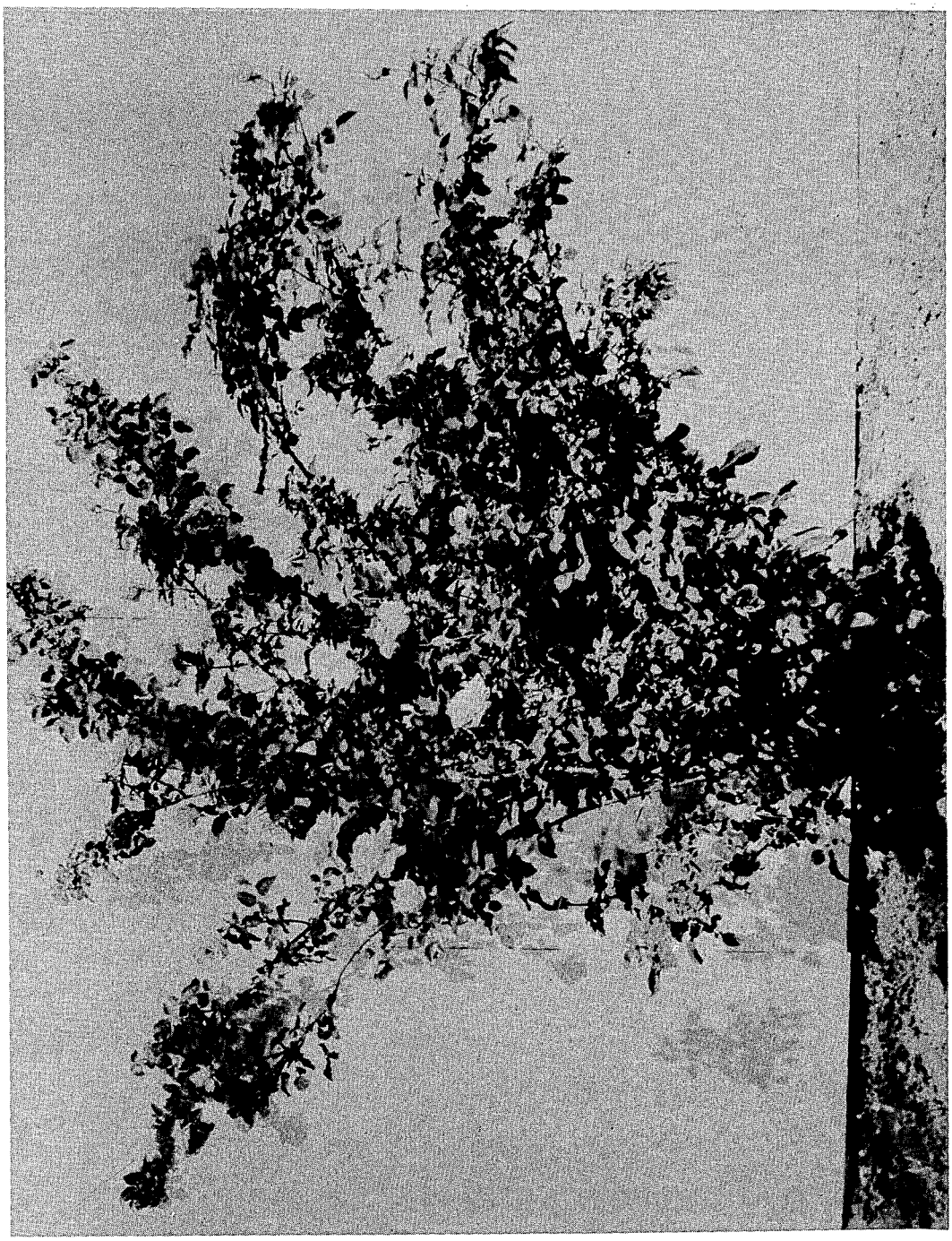
INVENTOR
R. V. Lindquist
BY Robb & Robb
ATTORNEYS United States Patent Office Plant Pat. 1,836

Patented May 26, 1959

1,836

ROSE PLANT

Robert V. Lindquist, Hemet, Calif., assignor to Hemet Wholesale, Hemet, Calif., a partnership Application October 31, 1958, Serial No. 771,171

1 Claim. (Cl. 47—61)

The present invention relates to a new and distinct variety of rose plant which originated as a sport of the variety "Tiffany" (Plant Patent 1,304) from which it is distinguished primarily by its climbing habit of growth and by a habit of producing flowers on stems shorter than those of the parent variety.

The new variety was discovered by me in the cultivated fields of my assignee, located near Hemet, California, where the variety "Tiffany" was being grown in large blocks. At the time of my discovery, my attention was attracted to the new variety by the unusually vigorous and climbing habit of a particular plant in the "Tiffany" block referred to above. Upon closer examination thereof, I found that the parent variety had sported, and I thereupon promptly took steps to preserve, asexually reproduce and observe the sport to determine whether its climbing habit was fixed and was transmissible by asexual reproduction. As a consequence, I have fully confirmed that the climbing habit is definitely fixed, as well as the shorter flower stem characteristic referred to above, and these characteristics are transmissible by asexual reproduction, as confirmed by buddings performed by me near Hemet, California.

So far as I am aware, the parent variety "Tiffany" has never before exhibited any tendency toward a climbing habit, having heretofore conformed to the usual habit of a bush rose of the hybrid tea type. Accordingly, the climbing habit of the sport, combined with its shorter flower stems, represents a unique and highly desirable combination of characteristics when considered together with its other characteristics which otherwise are generally similar to the characteristics of the parent variety. In view of these general similarities, excepting as noted in the foregoing, it is unnecessary to describe or illustrate the new variety in detail herein, but for convenience, the accompanying drawing illustrates in black-and-white a typical specimen plant of the new variety which shows its climbing habit of growth, as well as typical specimens of the flowers and foliage in different stages of development, as borne by the climbing plant.

Also, for convenience, the following description of my new variety is given, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Climbing; outdoor; sport; for cut flowers and for garden decoration.
Class: Climbing hybrid tea.
Parentage: Sport of "Tiffany."
Propagation: Holds its distinguishing characteristics through succeeding propagations by budding.

*Flower*

Locality where grown and observed: Hemet, California.
Flowers borne: Usually singly; on normal stems of medium length.

Quantity of bloom: From moderate to free, outdoors.
Continuity: Intermittent during growing season.
Fragrance: Penetrating. Nature—tea.
Bud:

*Peduncle.*—Average length; from 2 inches to 4 inches in length; average caliper; erect; few gland-tipped cilia and numerous prickles. Color—near Lettuce Green, Plate V (Ridgway).

*Before calyx breaks.*—Size—medium. Form—medium length; pointed; ovoid; with a conspicuous neck; with foliaceous appendages; with few gland-tipped cilia and glandular bloom on the surface of the bud; usually with foliaceous parts extending beyond the tip of the bud equal to ¼ or more of its length.

*As calyx breaks.*—Color—near Claret Rose, Plate 021, page 109 (Wilson).

*Sepals.*—Inner surface—with fine, woolly tomentum. Margins—a sepal has either both margins covered or both uncovered except for the 5th or odd sepal which has woolly tomentum on one margin only; sepals with glandular margins usually having foliaceous appendages, while margins without blands have woolly tomentum.

*As first petal opens.*—Size—from average to large. Form—from medium length to long; from pointed to ovoid. Color: outside—base near Dresden Yellow, Plate 64/1, page 64 (Wilson), tipped with near Uranium Green, Plate 63/2, page 63 (Wilson), shading to near Dresden Yellow, Plate 64/2, page 64 Wilson), with central part of petals near Rose Madder, Plate 23/2, page 23 (Wilson), and with margin near Rose Madder, Plate 23/1, page 23 (Wilson); inside—base near Dresden Yellow, Plate 64/1, page 64 (Wilson), becoming from near Rose Madder, Plate 23/2, page 23 (Wilson) to near Rose Madder, Plate 23/1, page 23 (Wilson) at margin.

*Opening.*—Opens up well; is not retarded from opening by hot, wet or dry weather.

Bloom:

*Size (when fully open).*—Large; from 4 inches to 5 inches.

*Petalage.*—From double to very double; from 25 to 30 petals, plus from 8 to 14 petaloids; arranged regularly.

*Form.*—High-centered at first, but becoming flat to cupped; petals being at first somewhat tightly flat to cupped and rolled outward, but later becoming somewhat tightly rolled outward at maturity.

Petals:

*Texture.*—Medium thickness; moderately leathery. Inside—slightly satiny. Outside—from slightly shiny to satiny.

*Shape.*—Outside—round, with apex flat. Intermediate—round, with apex from rounded to flat and with 1 or 2 notches. Inside—from nearly round to obovate; scalloped irregularly; with apex from rounded to flat and with 1 or 2 notches.

This description of a newly opened flower was made from a rose grown outdoors in the month of May at Hemet, California:

*Color.*—Outer petal: outside surface—base near Dresden Yellow, Plate 64/2, page 64 (Wilson), shading in center of petal to near Dresden Yellow, Plate 64/1, page 64 (Wilson), with distil parts of petals near Phlox Pink, Plate 625/3, page 77 (Wilson), shading to near Phlox Pink, Plate 625/2, page 77 (Wilson) at margin; inside surface—base near Dresden Yellow, Plate 64/1, page 64 (Wilson), shading to near Dresden Yellow, Plate 64/2, page 64 (Wilson), with distil parts of petals near Phlox Pink, Plate 625/3, page 77 (Wilson), shading to near Phlox Pink, Plate 625/2, page 77 (Wilson) at margin. Intermediate petal: outside surface—base near Dresden Yellow, Plate 64/2, page 64 (Wilson), shading to near Dresden Yellow, Plate 64/3, page 64 (Wilson), with distil part of margin of petals near Phlox Pink, Plate 625/3, page 77 (Wilson); inside surface—base near Dresden Yellow, Plate 64/1, page 64 (Wilson), shading to near Dresden Yellow, Plate 64/3, page 64 (Wilson), with center of petals near Phlox Pink, Plate 625/3, page 77 (Wilson), shading towards distil parts of petals to near Phlox Pink, Plate 625/2, page 77 (Wilson), and outer margin near Phlox Pink, Plate 625/1, page 77 (Wilson). Inner petal: outside surface—tip of base near Dresden Yellow, Plate 64/1, page 64 (Wilson), shading to near Dresden Yellow, Plate 64/3, page 64 (Wilson), with upper portion of petal near Neyron Rose, Plate 623/2, page 76 (Wilson), shading to near Neyron Rose, Plate 623/1, page 76 (Wilson) at margin; inside surface—base near Dresden Yellow, Plate 64/1, page 64 (Wilson), becoming near Neyron Rose, Plate 623/1, page 76 (Wilson), shading to near Neyron Rose, Plate 623, page 76 (Wilson) at margin.

This description was made from a rose that was open for 3 days indoors in the month of May, at Hemet, California:

*Color.*—Outer petal: outside surface—base near Dresden Yellow, Plate 64/2, page 64 (Wilson), shading to near Dresden Yellow, Plate 64/3, page 64 (Wilson), and becoming near Rose Pink, Plate 427/2, page 126 (Wilson); inside surface—base near Dresden Yellow, Plate 64/2, page 64 (Wilson), becoming near Phlox Pink, Plate 625/3, page 77 (Wilson), and shading to near Phlox Pink, Plate 625/2, page 77 (Wilson) toward margin. Inner petal: outside surface—base near Dresden Yellow, Plate 64/2, page 64 (Wilson), shading to near Dresden Yellow, Plate 64/3, page 64 (Wilson), and becoming near Phlox Pink, Plate 625/3, page 77 (Wilson), shading to near Phlox Pink, Plate 625/2, page 77 (Wilson) at margin; inside surface—base near Dresden Yellow, Plate 64/2, page 64 (Wilson), becoming near Phlox Pink, Plate 625/2, page 77 (Wilson) over remainder of petal.

*General color effect.*—Newly opened flower—from near Neyron Rose, Plate 623/1, page 76 (Wilson) to near Neyron Rose, Plate 623, page 76 (Wilson), with outer petals becoming much lighter in fully open flowers. 3-days open—near Phlox Pink, Plate 625/3, page 77 (Wilson).

*Behavior.*—Drop off cleanly, except for petaloids; is not particularly affected by cold, hot, wet or dry weather, except for minor changes in flower color.

*Flower longevity.*—On bush in garden—3 or 4 days in May. Cut roses grown outdoors and kept at living-room temperatures—3 or 4 days in May.

*Reproductive organs*

Stamens: Many; arranged regularly about pistils; a few mixed with petaloids.

Filaments: Medium length; occasionally has a filament with petaloid attached in place of anther; most with anthers. Color—near Primrose Yellow, Plate 601/1, page 65 (Wilson).

Anthers: Medium size; all open approximately at once. Color: upper side—near Saffron Yellow, Plate 7/1, page 7 (Wilson), along margin; under side—near Egyptian Buff, Plate 407, page 122 (Wilson).

Pollen: Moderately abundant. Color—near Saffron Yellow, Plate 7/2, page 7 (Wilson).

Pistils: Many; varying between 100 and 200, but approximately 150 on average.

Styles: Moderately uneven; average length; very thin; somewhat bunched.

Stigma: Color—near Naples Yellow, Plate 403, Page 403, Page 121 (Wilson).

Ovaries: Usually most enclosed in calyx, but some protruding therefrom.

Hips: Average length; turbinate; moderately smooth; walls thick and fleshy. Color—near Courge Green, Plate XVII (Ridgway).

Sepals: Permanent; long; spear-shaped; recurved. Color: inside—near Light Bice Green, Plate XVII (Ridgway), tinted slightly with near Corinthian Purple, Plate XXXVIII (Ridgway), modified by white tomentum; outside—near Light Bice Green, Plate XVII (Ridgway).

Seeds: Few; from 5 to 12 in number; usually medium size.

*Plant*

Foliage:

*Leaves.*—Compound of usually 3 to 7 leaflets; normal quantity; medium size; moderately heavy; somewhat leathery; semi-glossy.

*Leaflets.*—Shape—oval, with apex mucronate. Base—round. Margin—serrate.

*Color.*—Mature: upper surface—near Parsley Green, Plate 00962, page 193 (Wilson); under surface—near Asphodel Green, Plate XLI (Ridgway). Young: upper surface—near Spinach Green, Plate 0960/1, page 187 (Wilson), with some near Corinthian Purple, Plate XXXVIII (Ridgway), becoming more intense towards margin; under surface—near Corinthian Purple, Plate XXXVIII (Ridgway), with some near Spinach Green, Plate 0960/1, page 187 (Wilson) showing through.

*Rachis (the supporting stem of the compound leaf).*—Average size. Upper side—grooved; with some stipitate glands. Under side—moderately prickly.

*Stipules.*—Long; medium width; with points of medium length turning out at an angle of about 45°.

*Disease resistance.*—Average resistance to mildew, as determined from comparison with other varieties grown under comparable cultural conditions at Hemet, California.

Growth:

*Habit.*—Upright; climbing; much-branched.

*Growth.*—Vigorous.

*Canes.*—Heavy.

*Main stems.*—Color—near Chromium Green, Plate XXXII (Ridgway). Large prickles—from several to many; from medium length to long; almost straight; moderately broad base; color—varying from near Cinnamon, Plate XXIX (Ridgway) to near Cinnamon Brown, Plate XV (Ridgway), with some near Hessian Brown, Plate XIII (Ridgway) near base on some thorns. Small prickles—very few; color—near Cinnamon, Plate XXIX (Ridgway). Hairs—none.

*Branches.*—Color—near Chromium Green, Plate XXXII (Ridgway). Large prickles—from several to many; medium length; almost straight; moderately narrow base; color—near Cinnamon Brown, Plate XV (Ridgway). Small prickles—several; color—near Russett, Plate XV (Ridgway). Hairs—none.

*New shoots.*—Color—near Light Bice Green, Plate XVII (Ridgway). Large prickles—from several to many; hooked slightly downward; narrow base of medium length; color—near Biscay Green, Plate XVII (Ridgway), shaded at base with near Deep Hellebore Red, Plate XXXVIII (Ridgway). Small prickles—few; color—near Biscay Green, Plate XVII (Ridgway), shaded at base with near Deep Hellebore Red, Plate XXXVIII (Ridgway). Hairs—few glandular-tipped hairs.

I claim:

A new and distinct variety of rose plant of the climbing hybrid tea class, substantially as herein shown and described, characterized particularly as to novelty by being generally similar to its parent variety "Tiffany" (Plant Patent No. 1,304), but being essentially different therefrom by a climbing habit of growth, and a habit of bearing flowers on stems shorter than those of said parent variety.

No references cited.